(12) United States Patent
Silverman

(10) Patent No.: US 7,869,961 B2
(45) Date of Patent: *Jan. 11, 2011

(54) SPATIAL PROFILING OF PROTEINS USING HYDROPHOBIC MOMENTS

(75) Inventor: Benjamin D. Silverman, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/870,081

(22) Filed: Oct. 10, 2007

(65) Prior Publication Data

US 2008/0086291 A1    Apr. 10, 2008

Related U.S. Application Data

(62) Division of application No. 09/818,461, filed on Mar. 27, 2001, now Pat. No. 7,343,246.

(60) Provisional application No. 60/245,396, filed on Nov. 2, 2000.

(51) Int. Cl.
*G06F 17/11* (2006.01)
*G06F 17/50* (2006.01)
*G06F 19/00* (2006.01)

(52) U.S. Cl. .......................... 702/19; 702/27

(58) Field of Classification Search ....................... None
See application file for complete search history.

(56) References Cited

U.S. PATENT DOCUMENTS

| 6,790,773 B1 | 9/2004 | Drewery et al. |
| 7,343,246 B2 * | 3/2008 | Silverman ..................... 702/19 |
| 7,499,805 B2 * | 3/2009 | Athma et al. .................. 702/19 |
| 2005/0095846 A1 | 5/2005 | Basol |
| 2005/0181598 A1 | 8/2005 | Kailasam |
| 2006/0199372 A1 | 9/2006 | Chung et al. |
| 2007/0238288 A1 | 10/2007 | Suzuki |

OTHER PUBLICATIONS

Eisenberg et al., Faraday Symposia of the Chemical Society, 1982, 17, 109-120.*
Karplus et al Protein Science, 6, 1302-1307, 1997.*
Database CaPlus, DN 103:84898., Bar-Ol et al., Archives of Microbiology, 1985, 142(1), pp. 21-27.*
Silverman, D, Proc Natl Acad Sci U S A Apr. 24, 2001; 98(9): 4996-5001.*
Cornette et al J. Mol Biol., 1987,195,659-685.*

* cited by examiner

*Primary Examiner*—Michael Borin
(74) *Attorney, Agent, or Firm*—Ryan, Mason & Lewis, LLP

(57) ABSTRACT

Generally, the present invention provides a number of procedures to spatially profile proteins by using hydrophobic moments. In all procedures, a hydrophobicity distribution of a protein is shifted and normalized. In one procedure, a shape or profile of a curve of a second-order moment of hydrophobicity is determined. A second procedure involves determining one or more ratios, such as the ratio of a distance at which the second order moment of hydrophobicity vanishes to the distance at which a zero-order moment of hydrophobicity vanishes. The distance at which a peak occurs in a profile of the zero- or second-order moment of hydrophobicity can also be used for comparison. For many of these procedures, a surface or profiling contour can be chosen and used to accumulate hydrophobicities and to determine the moments. These procedures can be combined to provide a good mathematical determination of whether a protein belongs to a particular class of proteins.

24 Claims, 12 Drawing Sheets

| residue | consensus |
|---|---|
| Arginine | -1.76 |
| Lysine | -1.10 |
| Aspartic acid | -0.72 |
| Glutamine | -0.69 |
| Asparagine | -0.64 |
| Glutamic acid | -0.62 |
| Histidine | -0.40 |
| Serine | -0.26 |
| Threonine | -0.18 |
| Proline | -0.07 |
| Tyrosine | 0.02 |
| Cysteine | 0.04 |
| Glycine | 0.16 |
| Alanine | 0.25 |
| Methionine | 0.26 |
| Tryptophan | 0.37 |
| Leucine | 0.53 |
| Valine | 0.54 |
| Phenylalanine | 0.61 |
| Isoleucine | 0.73 |

| pdb id | number | pdb id | number |
| --- | --- | --- | --- |
| 1ORC | 63 | 1BN1-α | 257 |
| 1CDZ | 96 | 2DRI | 271 |
| 1NEU | 115 | 1AUA | 296 |
| 1DZO-α | 120 | 1LDM | 329 |
| 1A4V | 123 | 1FSZ | 334 |
| 1AT0 | 125 | 1UBY | 348 |
| 1PDO | 129 | 1A26 | 351 |
| 2SNS | 141 | 1PHC | 405 |
| 1CQ2-α | 153 | 1BGV | 449 |
| 1PHR | 154 | 3PBG | 468 |
| 1CTQ | 166 | 1GAI-α | 472 |
| 121P | 166 | 3COX-α | 500 |
| 1DZV | 206 | 1FEH | 574 |
| 1AUN | 208 | B_1FJF-α | 234 |
| 1LBU | 213 | C_1FJF-α | 206 |
| 2ACT | 218 | D_1FJF-α | 208 |
| 1AKZ | 223 | | |

FIG. 4

| d(Ang.) | $n_d$ | $H_0(d)$ | $H_2(d)$ |
|---|---|---|---|
| 4 | 1 | 0.288 | 2.62 |
| 5 | 1 | 0.288 | 2.62 |
| 6 | 5 | 0.607 | 16.86 |
| 7 | 7 | 0.657 | 22.28 |
| 8 | 7 | 0.657 | 22.28 |
| 9 | 13 | 0.842 | 45.1 |
| 10 | 16 | 0.779 | 44.53 |
| 11 | 24 | 0.738 | 54.44 |
| 12 | 27 | 0.75 | 60.8 |
| 13 | 40 | 0.675 | 67.57 |
| 14 | 53 | 0.645 | 75.13 |
| 15 | 63 | 0.606 | 76.76 |
| 16 | 77 | 0.574 | 81.75 |
| 17 | 89 | 0.51 | 74.23 |
| 18 | 101 | 0.487 | 77.2 |
| 19 | 114 | 0.403 | 58.94 |
| 20 | 138 | 0.328 | 47.12 |
| 21 | 156 | 0.266 | 32.14 |
| 22 | 168 | 0.211 | 12.68 |
| 23 | 184 | 0.127 | -21.54 |
| 24 | 200 | 0.063 | -49.53 |
| 25 | 208 | 0.048 | -54.96 |
| 26 | 215 | 0.029 | -64.99 |
| 27 | 218 | 0.023 | -67.81 |
| 28 | 220 | 0.016 | -72.45 |
| 29 | 221 | 0.008 | -77.65 |
| 30 | 223 | 0 | -84.67 |

FIG. 6

| d(Ang.) | $n_d$ | $H_0(d)$ | $H_2(d)$ |
|---|---|---|---|
| 4 | 1 | -0.421 | -3.84 |
| 5 | 1 | -0.421 | -3.84 |
| 6 | 5 | -0.486 | -13.50 |
| 7 | 7 | -0.518 | -17.11 |
| 8 | 7 | -0.518 | -17.11 |
| 9 | 13 | -0.238 | -6.41 |
| 10 | 16 | -0.187 | -3.92 |
| 11 | 24 | -0.025 | 8.41 |
| 12 | 27 | 0.011 | 11.64 |
| 13 | 40 | 0.041 | 12.76 |
| 14 | 53 | 0.040 | 10.66 |
| 15 | 63 | 0.058 | 14.02 |
| 16 | 77 | -0.074 | -17.48 |
| 17 | 89 | -0.003 | 1.23 |
| 18 | 101 | -0.008 | -0.24 |
| 19 | 114 | -0.024 | -5.92 |
| 20 | 138 | -0.021 | -4.35 |
| 21 | 156 | -0.009 | -0.19 |
| 22 | 168 | -0.008 | -0.19 |
| 23 | 184 | 0.004 | 5.15 |
| 24 | 200 | 0.009 | 7.99 |
| 25 | 208 | 0.018 | 13.58 |
| 26 | 215 | 0.034 | 23.84 |
| 27 | 218 | 0.024 | 16.36 |
| 28 | 220 | 0.015 | 10.03 |
| 29 | 221 | 0.011 | 6.64 |
| 30 | 223 | 0.000 | -2.56 |

FIG. 8

| pdb id | $d_-/d_0$ | Rt | spherical | pdb id | $d_-/d_0$ | Rt | spherical |
|---|---|---|---|---|---|---|---|
| 1ORC | 14/20 | 0.70 | 0.68 | 1BN1-α | 23/30 | 0.8 | 0.72 |
| 1CDZ | 18/23 | 0.78 | 0.73 | 2DRI | 31/37 | 0.8 | 0.94 |
| 1NEU | 18/28 | 0.64 | 0.64 | 1AUA | 28/34 | 0.8 | 0.79 |
| 1DZO-α | 21/29 | 0.72 | 0.68 | 1LDM | 30/37 | 0.8 | 0.71 |
| 1A4V | 20/29 | 0.69 | 0.63 | 1FSZ | 25/34 | 0.7 | 0.70 |
| 1AT0 | 19/25 | 0.76 | 0.74 | 1UBY | 30/43 | 0.70 | 0.70 |
| 1PDO | 18/23 | 0.78 | 0.70 | 1A26 | 29/41 | 0.71 | 0.68 |
| 2SNS | 20/28 | 0.71 | 0.63 | 1PHC | 29/38 | 0.8 | 0.73 |
| 1CQ2-α | 17/25 | 0.68 | 0.70 | 1BGV | 30/38 | 0.8 | 0.76 |
| 1PHR | 19/26 | 0.73 | 0.69 | 3PBG | 29/37 | 0.8 | 0.77 |
| 1CTQ | 19/25 | 0.76 | 0.79 | 1GAI-α | 27/37 | 0.7 | 0.66 |
| 121P | 19/25 | 0.76 | 0.75 | 3COX-α | 30/38 | 0.8 | 0.68 |
| 1DZV | 26/34 | 0.76 | 0.74 | 1FEH | 36/51 | 0.7 | 0.63 |
| 1AUN | 22/29 | 0.76 | 0.71 | B_1FJF-α | 25/43 | 0.6 | 0.49 |
| 1LBU | 20/29 | 0.69 | 0.58 | C_1FJF-α | 26/36 | 0.7 | 0.73 |
| 2ACT | 22/28 | 0.79 | 0.70 | D_1FJF-α | 29/33 | 0.9 | 0.81 |
| 1AKZ | 23/30 | 0.77 | 0.72 | | | | |

FIG. 11

SPATIAL PROFILING OF PROTEINS USING HYDROPHOBIC MOMENTS

CROSS REFERENCE TO RELATED APPLICATIONS

This application is a divisional application of U.S. patent application Ser. No. 09/818,461, filed Mar. 27, 2001 now U.S. Pat. No. 7,343,246, which claims the benefit of U.S. Provisional Application No. 60/245,396, filed Nov. 2, 2000 incorporated by reference herein.

FIELD OF THE INVENTION

The present invention relates to the mathematical analysis of proteins and, more particularly, relates to the spatial profiling of proteins using hydrophobic moments.

BACKGROUND OF THE INVENTION

Proteins may be thought of as string with beads on it. Each bead has a particular color. For many proteins, there are 20 colors, or 20 different beads. The string folds up in a certain way, which means that it ends up with a certain series of folds. When profiling a protein, researchers attempt to determine the order of the colors of the beads and where the beads are in three-dimensional space. These locations are important because all of the bodily functions depend on this three-dimensional structure. An important problem is determining how hundreds of thousands of proteins fold.

Many proteins are globular and form in an intracellular environment or plasma, which are both aqueous environments. For these proteins, it can be assumed that there are only two colors, blue and red. Blue beads (called "hydrophobic") do not like water and red beads (called "hychophilic") are attracted to water. When these types of globular proteins fold up, all of the blue beads get in the center and the red beads are on the outside of the protein. Consequently, the residues that like water are on the outside and the residues that do not like water are on the inside. A protein formed in this manner will have a hydrophobic core and a hydrophilic exterior.

The structure of globular proteins can actually be quite complex, and contain substructures such as beta sheets, beta strands, alpha-helices, and other helices. Because the structure of the protein affects the way that the protein interacts with its environment (and vice versa), protein structures have been studied in detail A computational technique for studying proteins includes mathematically modeling protein structure to determine primary, secondary, tertiary, and even quaternary protein structures.

Many of these techniques examine details associated with proteins, such as determining exactly where residues are or the exact order of residues. Few of these techniques are suitable for analyzing an entire protein. Even fewer of the these techniques can accurately determine whether a man-made protein structure is or could be a real protein.

Thus, what is needed is a better way of quantifying and analyzing protein structure and a better way to determine if an example protein structure is or could be a real protein.

SUMMARY OF THE INVENTION

Generally, the present invention provides a number of procedures to spatially profile proteins by using hydrophobic moments. In all procedures, a hydrophobicity distribution of a protein is shifted and normalized. This allows better quantitative comparisons of proteins. In one procedure, a shape or profile of a curve of a second-order moment of hydrophobicity is determined. This shape can then be used to determine if an example protein belongs to a particular class of proteins, such as globular proteins. A second procedure involves determining one or more ratios, such as the ratio of a distance at which the second order moment of hydrophobicity vanishes to the distance at which a zero-order moment of hydrophobicity vanishes. The distance at which a peak occurs in a profile of the zero- or second-order moment of hydrophobicity can also be used for comparison. These techniques also help to determine if a protein belongs to a globular or other class of proteins. For many of these techniques, a surface or profiling contour can be chosen and used to accumulate hydrophobicities and to determine the moments. These procedures can be combined to provide a good mathematical determination of whether a protein belongs to a particular class of proteins. For globular proteins in particular, the present invention reveals that many globular proteins exhibit similar structural characteristics. This result may be used to easily determine if a decoy protein (a man-made exemplary protein) is a globular protein or a poor structural imitation.

A more complete understanding of the present invention, as well as further features and advantages of the present invention, will be obtained by reference to the following detailed description and drawings.

BRIEF DESCRIPTION OF THE DRAWINGS

FIG. 4 is a table containing proteins from the Protein Data Bank (PDB) that were used in experiments involving an embodiment of the present invention;

FIG. 6 is a profile showing the second- and zero-order moments, determined through use of an embodiment of the present invention, for the 1AKZ protein;

FIG. 8 is a table that results when the 1AKZ structure is fixed and hydrophobic values are randomly shuffled;

FIG. 11 shows a table of results, obtained through use of an embodiment of the present invention, for a number of proteins from the PDB;

DETAILED DESCRIPTION OF PREFERRED EMBODIMENTS

Figure 1:
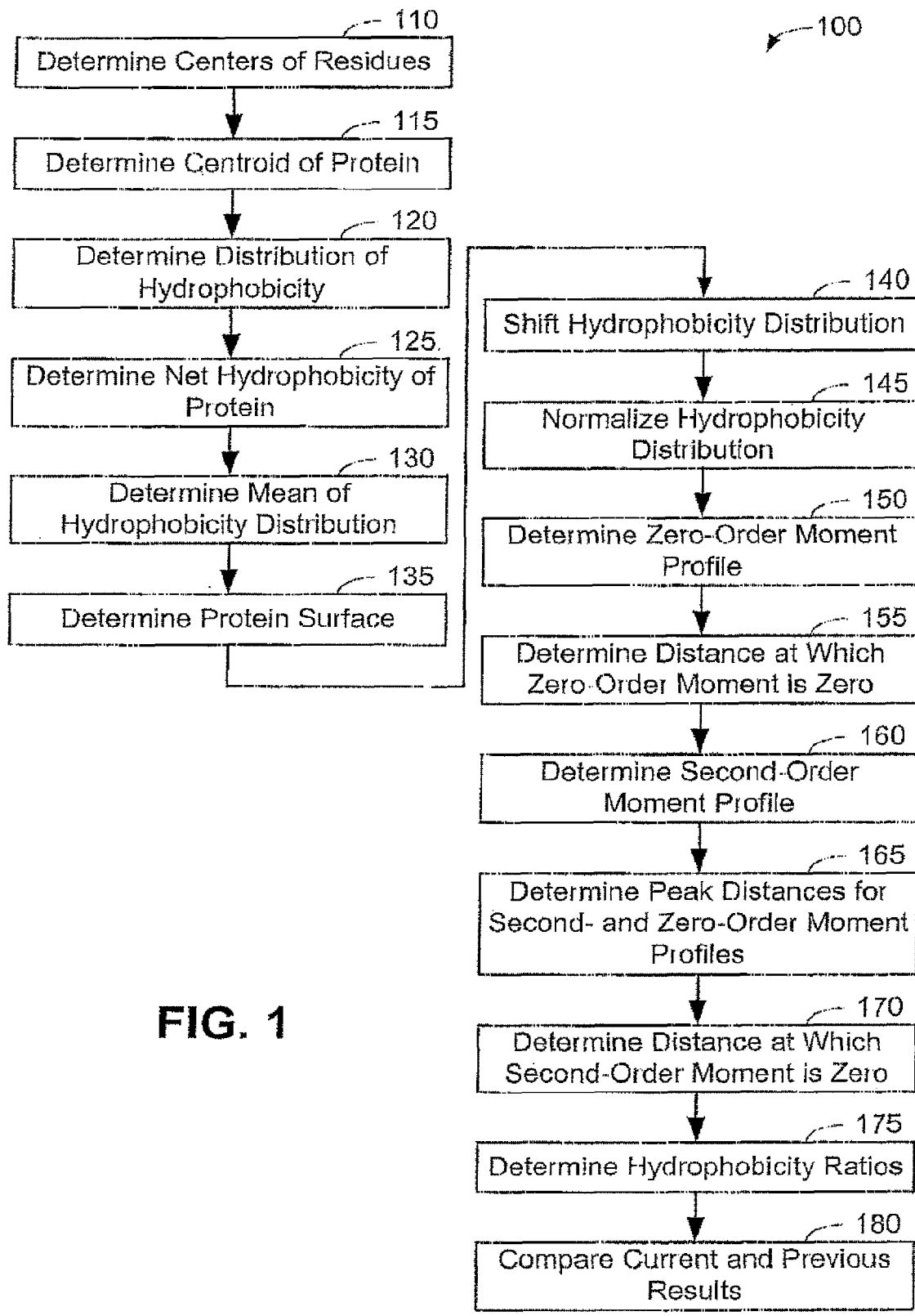
FIG. 1 is a flowchart of a method for spatially profiling proteins in accordance with one embodiment of the present invention.

The present invention provides a tool for probing protein structure. This tool may be used in such situations as protein folding, dynamic protein modeling or analysis of protein structure. The present invention may be used to analyze any protein but is particularly useful for analyzing proteins that form in an aqueous environment, such as globular proteins. It turns out, as will be discussed in more detail below, that globular proteins exhibit certain characteristics that can be determined by the present invention. These characteristics can be used to analyze a protein or decoy (a man-made protein) to see if it is a globular protein. Transmembrane proteins will have a different profile signature, but may also be analyzed by the present invention.

Because globular proteins form in an aqueous environment, they have a hydrophobic core and a hydrophilic exterior. A hydrophobicity scale can be used to determine the hydrophobicity distribution of a protein. A hydrophobicity value is a value that indicates the degree to which a residue is attracted to or repelled by water. The resultant hydrophobicity distribution can be shifted and normalized, which places each protein with mathematical basis for comparison. Without shifting the hydrophobicity distribution, the ability to compare different proteins is significantly degraded. If the hydrophobicity distribution is shifted but not normalized, the ratios disclosed herein can still be compared. However, values of the moments cannot be compared.

After shifting and/or normalizing the hydrophobicity distribution, the adjusted zero- and second-order moments of the hydrophobicity distribution can be determined. The zero- and second-order moments are "adjusted" because they use a hydrophobicity distribution that is shifted or shifted and scaled. The shape or profile of the adjusted second-order moment can be used to determine if a protein is globular. All globular proteins studied to date exhibit a characteristic profile such that the adjusted second-order moment rises from zero to a high positive value, then passes through zero and becomes strongly negative. There is generally only one zero crossing after the high positive value, and the profile becomes strongly negative after the zero crossing. Any protein that does not exhibit this profile most likely is not a globular protein.

Another technique that can be used to distinguish globular proteins from other proteins or decoys is the determination of a ratio of the distance at which the adjusted second-order moment of hydrophobicity vanishes and the distance at which the adjusted zero-order moment of the hydrophobicity vanishes (or vice versa). Another ratio that can be determined is a ratio of a distance at which a peak occurs in a profile of the zero-order moment of hydrophobicity and a distance at which the zero-order moment of hydrophobicity vanishes. Yet another ratio is a ratio between a distance at which a peak occurs in a profile of the second-order moment of hydrophobicity and the distance at which the second-order moment of hydrophobicity vanishes. For all globular proteins, both peaks of the zero- and second-order moments occur at the same distance from the centroid of the protein. Globulat proteins tend to exhibit a certain range of these distance ratios. If a protein or decoy has a hydrophobicity ratio that is not within the range, then the protein or decoy is likely not a globular protein.

The "distance" discussed in the last paragraph is determined with reference to the centroid of the protein, which is the center of mass of the protein when each of residue is assigned unit mass. Additionally, a surface is necessary to determine the cumulative moments. A good choice of a surface for globular proteins is an ellipsoidal surface. The ellipsoidal surface is used to determine the cumulative moment at a particular distance from the centroid. The surface defines a volume that contains the hydrophobicity distribution of amino acid residues.

Although the primary emphasis herein is placed on globular proteins, the present invention may be used to analyze other proteins, such as extracellular or transmembrane proteins, as well. For these proteins, suitable surfaces, such as spheres or cylinders, may be utilized.

Referring now to FIG. 1, this figure shows a flow chart of a method 100 for spatially profiling proteins by using hydrophobic moments. Method 100 is used to analyze a protein, analyze many proteins and/or determine if an exemplary protein belongs to a class of proteins that have already been analyzed using method 100. Method 100 begins when the centers of residues are determined (step 110). The centers of residues can be either the α-carbon location of the residue or the centroid of the residue. The centroid of a residue can be determined by determining the center of mass of the residue, when each atom is assigned a location and the location is assigned a mass value of one. It is also possible to mix centroids, α-carbon locations (i e, use the α-carbon location of one residue and the centroid of another residue), and centroids of residues that have atoms missing.

The centroid of the protein (step 115) is determined as the centroid of residue centroids.

Figures 2, 3:
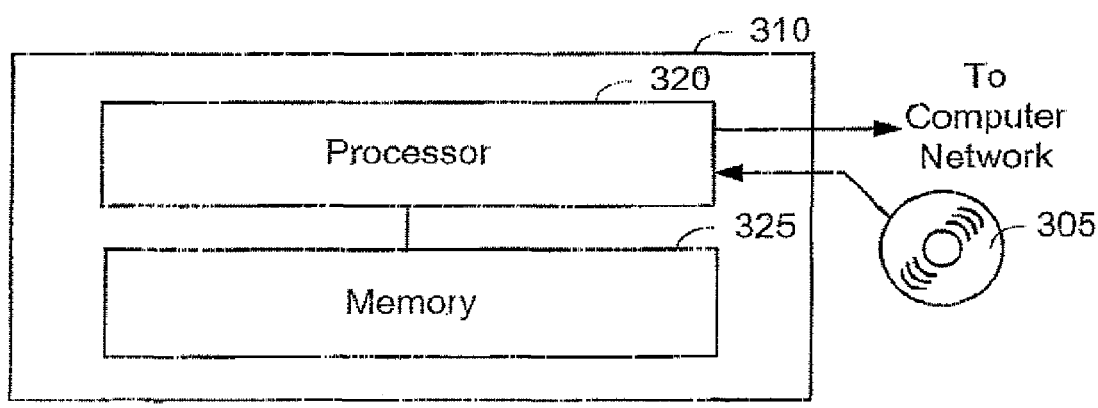
FIG. 2 is a table of the hydrophobicity values for amino acids.
FIG. 3 is a system for spatially profiling proteins in accordance with one embodiment of the present invention.

In step 120, the hydrophobicity distribution is determined. Each residue is assigned a hydrophobicity consensus value $h_i$. In this disclosure, a residue and an amino acid will be treated as being fungible. A representative table of hydrophobicity values is shown in FIG. 2 and discussed below. The zero-order moment of the amino acid distribution of protein hydrophobicity is:

$$H_0 = \sum_i h_i \qquad (\text{Eq. 1})$$

It should be noted that this is also the net hydrophobicity of the protein (step 120 of FIG. 1).

The first-order moment of the hydrophobicity distribution is:

$$\vec{H}_1 = \sum_i h_i \vec{r}_i, \qquad (\text{Eq. 2})$$

where $\vec{r}_i$ is a vector to the centroid of the $i^{th}$ amino acid residue with hydrophobicity consensus value $h_1$. The sum is over all n amino acid residues. Since the zero-order moment, $H_0$, or net hydrophobicity of the protein, is generally non-vanishing, the first-order moment will depend upon the origin of the calculation. In connection with the calculated moments of α-helices, Eisenberg (see Eisenberg et al., Faraday Symp. Chem. Soc., 17, pp. 109-120, 1982; and Eisenberg et al., Nature, p. 299, 371-374, 1982, the disclosures of which are incorporated herein by reference) had pointed out that the first-order moment would be invariant if hydrophobicity differences about the mean, $\bar{h}$, were calculated with respect to an arbitrary origin, as the following equation illustrates:

$$\vec{H}_1 = \sum_i (h_i - \bar{h})\vec{r}_i \quad \text{(Eq. 3)}$$

with $\bar{h}=H_0/n$. Using the protein centroid as the origin of the moment expansion yields this invariant value of the first-order moment, namely:

$$\vec{H}_1 = \sum_i h_i(\vec{r}_i - \vec{r}_c), \text{ where} \quad \text{(Eq. 4)}$$

$$\vec{r}_c = (1/n)\sum_i \vec{r}_i \quad \text{(Eq. 5)}$$

The first-order moment calculated about the centroid of the protein is, therefore, a measure of first-order hydrophobic imbalance about the mean. With the inclusion of values of the solvent accessible surface area, $s_i$, fox each of the residues, the surface exposed first-order hydrophobic moment imbalance about the entire protein can then be written:

$$\vec{H}_1^s = \sum_i h_i s_i (r_i - r_c) \quad \text{(Eq. 6)}$$

This could provide useful information with respect to the three-dimensional spatial affinity of the tertiary protein structure and external structures with which it might interact. Thus, these equations provide insight into protein structures. However, this would not profile the hydrophobicity distribution within the protein interior.

Second-order moments provide the capability of spatially profiling the hydrophobicity distribution of amino acid residues. Profiling the distribution of hydrophobicity requires the choice of a profiling shape. Proteins come with all sorts of overall shapes. To profile, one must choose a particular reference point (the centroid), an appropriate coordinate system (the principal axes of geometry) and a shape representative of the protein (such as an ellipsoidal shape for a globular protein). A representation that is the simplest generalization of the shape of a globular protein is an ellipsoidal representation. This representation can be generated from the molecular moments-of-geometry, i.e., moments-of-inertia for which all amino acid residue centroids are weighted by unity instead of by residue mass. The moments of geometry are obtained as eigenvalues of the following moment-of-geometry matrix written in dyadic notation:

$$\tilde{M}_2 = \sum_i (\tilde{1}|\vec{r}_i - \vec{r}_c|^2 - (\vec{r}_i - \vec{r}_c)(\vec{r}_i - \vec{r}_c)), \quad \text{(Eq. 7)}$$

where $\tilde{1}$ is the unit dyadic. The calculation is performed with the centroid (determined by using the amino acid centroids) of the protein as origin. The moments-of-geometry are designated $g_1$, $g_2$, and $g_3$, with $g_1 < g_2 < g_3$. The ellipsoidal representation generated by these moments is written as:

$$x^2 + g'_2 y^2 = g'_3 z^2 = d^2 \quad \text{(Eq 8)}$$

with $g'_2 = g_2/g_1$ and $g'_3 = g_3/g_1$. The coordinates, x, y, z, are written in the lame of the principal-geometric-axes Equation 8 determines a surface (step 135) that can be used to profile the moments of the hydrophobicity distribution.

The ellipsoidal surface obtained by the choice of a particular value of d enables the collection of the values of hydrophobicity for all amino acid residues of number, $n_d$, lying within this surface. The consensus hydrophobicity scale of FIG. 2, discussed in more detail below, can be used to assign individual hydrophobicities for each residue.

The hydrophobicity distribution arises from the spatial distribution of residues and their assigned values of hydrophobicity. The distribution of amino acid hydrophobicity is, however, shifted (step 140) such that the net hydrophobicity of each protein vanishes. This is done by subtracting the average hydrophobicity from each value in the hydrophobicity distribution. Thus, when the surface described by d encompasses all of the residues, the shifted hydrophobicity distribution will yield a net hydrophobicity value of zero.

It should be noted that it is not necessary to zero the net hydrophobicity when the last residue is collected. Optionally, one could profile the protein by zeroing out the zero-order moment (which is an indication of the net hydrophobicity up until a certain distance) at a location in the protein interior.

Such shifting of the values of amino acid hydrophobicity eliminates the zero-order moment from the distribution and, consequently, the dependence of the second-order moment upon differences in net protein hydrophobicity. This provides a basis for comparison of the hydrophobic moment profiles of the different proteins and, consequently, a basis for comparison of their hydrophobic ratios.

The distribution is then optionally, but preferably, normalized (step 145) to yield a standard deviation of one. This step enables comparison of the moment magnitudes of different proteins.

The average hydrophobicity per residue collected within the ellipsoidal surface specified by d is then written (step 150):

$$H_0^d(d) = (1/n_d)\sum_{i \leq d} h'_i = (1/n_d)\sum_{i \leq d} (h_i - \bar{h})/ < h_j - \bar{h})^2 >^{1/2}. \quad \text{(Eq. 9)}$$

Equation 9 is one way to create an adjusted zero-order hydrophobic moment The superscript, d, indicates that the moment has been divided by the number of residues, $n_d$. Dividing by the number of residues is not necessary, but can be used to aid comparisons. The prime designates the value of hydrophobicity of each residue after shifting and normalizing the distribution. The term $(h_i - \bar{h})$ shifts the hydrophobicity distribution, while the term $<h_j - \bar{h})_2>^{1/2}$ normalizes the distribution. The subscript, j, and the brackets, "< >", refer to an average over a different index from the subscript, i. When the value of the surface d is just sufficiently large enough to collect all of the residues, the net hydrophobicity of the protein vanishes (step 155). This value of d assigns a "protein surface" as a location of common reference. Calculations that are performed for each of the proteins, as discussed in the Example section below, will examine increasing the value of d until all residues have been collected and the mean hydrophobicity vanishes.

The value of the second-order ellipsoidal moment per residue (step 160), from residues lying within the ellipsoidal surface specified by d is written:

$$H_2^d(d) = (1/n_d)\sum_{i \le d} h_i'(x_i^2 + g_2'y_i^2 + g_3'z_i^2) = (1/n_d)\sum_{i \le d} h_i'd_i^2 \quad \text{(Eq. 10)}$$

Equation 10 is one way to create an adjusted second-order hydrophobic moment. When all residues fall within the ellipsoidal surface and are collected, the following results:

$$H_2^d = (1/n_d)\sum_i h_i'd_i^2 = (1/n)\sum_i (h_i/<h_j - h>^2)^{1/2})(d_i^2 - \bar{d}^2), \quad \text{(Eq. 11)}$$

where $$\bar{d}^2 = (1/n)\Sigma d_i^2. \quad \text{(Eq 12)}$$

The values of $H_0^d$ and $H_2^d$ are calculated for each protein with increasing values of the surface defined by d.

Once the zero- and second-order hydrophobic moments have been determined, the distances at which peaks occur for the profiles of these moments may be determined (step 165). The distances of the peaks are preferably determined as being distances from the centroid of the protein. Some exemplary peaks and distances are described below.

In step 170, the distance is determined at which the second-order hydrophobic moment becomes zero. The distance d is the value of d for which $H_2^d$ has changed sign, becoming negative, and do the value for which Hod vanishes. The protocol that, for d. to be chosen, all values of $H_2^d$ at larger values of d must be negative, seems to be a quick estimate of when the second-order hydrophobic moment vanishes. A more accurate estimate would choose the value of d for which the second-order moment was the smallest.

In step 175, various hydrophobic ratios are determined. One possible ratio is the ratio between d. and $d_0$ (i.e., R equal to $d/d_0$). Another ratio is the ratio between a distance at which a peak of the zero-order moment of hydrophobicity occurs ($d_{0p}$) and a distance at which the zero-order moment of hydrophobicity vanishes (i.e., R equal to $d_{0p}/d_0$). A third ratio is the ratio of a distance at which a peak of the second-order moment of hydrophobicity occurs ($d_{2p}$) and the distance at which the zero-order moment of hydrophobicity vanishes (i.e., R equal to $d_{2p}/d_0$). The latter two ratios, as seen and discussed below, are equal.

For globular proteins, these ratios should be comparable and act as discriminative devices, which can include or exclude proteins from a set of representative globular proteins.

In step 180, results from examining the current protein can be compared with results determined previously. This step allows a set of proteins to be determined and a general profile that matches each of the profiles for the zero- and/or second-order hydrophobic moments to be determined. Ranges of ratios for the set of proteins can also be determined. If the protein being examined has profiles that are of a shape similar to the general profile, then the current protein is assumed to belong to the class of proteins defined by the set of proteins. Similarly, if the ratios for the current protein are within a predetermined amount from the range of ratios obtained for the set of proteins, then the current protein is assumed to belong to the class of proteins defined by the set of proteins.

In this manner, either single proteins or a set of proteins may be examined and profiled or compared with the profiles or ratios determined from a training set of proteins.

Referring now to FIG. 2, this figure shows the consensus values of hydrophobicity for the twenty residues. These hydrophobicity values used for each of the examples in the Examples section below were taken from this table.

Turning now to FIG. 3, an exemplary system 300 is shown that could be used to perform the methods and apparatus of the present invention. System 300 comprises a compact disk 305, a computer system 310 that itself comprises processor 320 and memory 325, and a connection to a network (the network is not shown in FIG. 3). Memory 325 comprises some or all of the elements used to per form the embodiments of the present invention. As such, memory 325 will configure the processor 320 to implement the methods, steps, and functions disclosed herein. The memory 325 could be distributed or local and the processor 320 could be distributed or singular. The memory 325 could be implemented as an electrical, magnetic or optical memory, or any combination of these or other types of storage devices. Moreover, the term "memory" should be construed broadly enough to encompass any device or medium where information can be read from or written to an address in the addressable space accessed by processor 320. With this definition, information on a network is still within memory 325 of system 300 because the processor 320 can retrieve the information from the network. It should be noted that each distributed processor that makes up processor 320 will generally contain its own addressable memory space.

It should also be noted that computers system 310 could be an application-specific integrated circuit that performs some or all of the steps and functions discussed herein.

As is known in the art, the methods and apparatus discussed herein may be distributed as an article of manufacture (such as compact disk 305) that itself comprises a computer readable medium having computer readable program code embodied thereon. The computer readable program code is operable, in conjunction with a computer system, to carry out all or some of the steps to perform the methods or create the apparatuses discussed herein. The computer readable medium may be a recordable medium (e.g., floppy disks, hard drives, compact disks, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable program code is any mechanism for allowing a computer to read instructions and data, such as magnetic variations on a magnetic medium or height variations on the surface of compact disk 305.

What has been shown so fax is a tool for probing proteins and revealing structures of proteins that have not been determined before. This tool also provides better comparisons between proteins than what has come before. Because the benefits of the present invention are hard to envision when equations are solely used, the following Examples section provides a more visual and succinct description of results obtained by using the present invention.

EXAMPLES

Now that the methods of the present invention have been presented, experimental results will be presented. For the experimental results, protein structures were selected by keyword searches of the Protein Data Bank (PDB) and by examination of entries in different SCOP classes. For more discussion on the latter; see Murzin et al., Journal of Molecular Biology 247, 536-540, 1995, the disclosure of which is incorporated herein by reference. The objective was to choose a selection representative of different sizes and different classes. Thirty protein structures were chosen in this manner. For an internal check, two of the proteins chosen included 1CTQ and 121P, the same protein with independently determined structures. Three additional proteins were also chosen from the recently determined structure of the 30S ribosomal subunit. For more information about the structure of the 30S ribosomal subunit, see Wimberly et al. Nature 407, 327-339, 2000, the disclosure of which is incorporated herein by reference. The PDB identifications (IDs) and number of amino acid residues for each are listed in FIG. 4. Finally, fourteen simple decoys as well as their native structures were also chosen for examination. For more discussion of these decoys, see Holm et al, Journal of Molecular Biology 225, 93-105, 1992, the disclosure of which is incorporated herein by reference.

Figure 5:
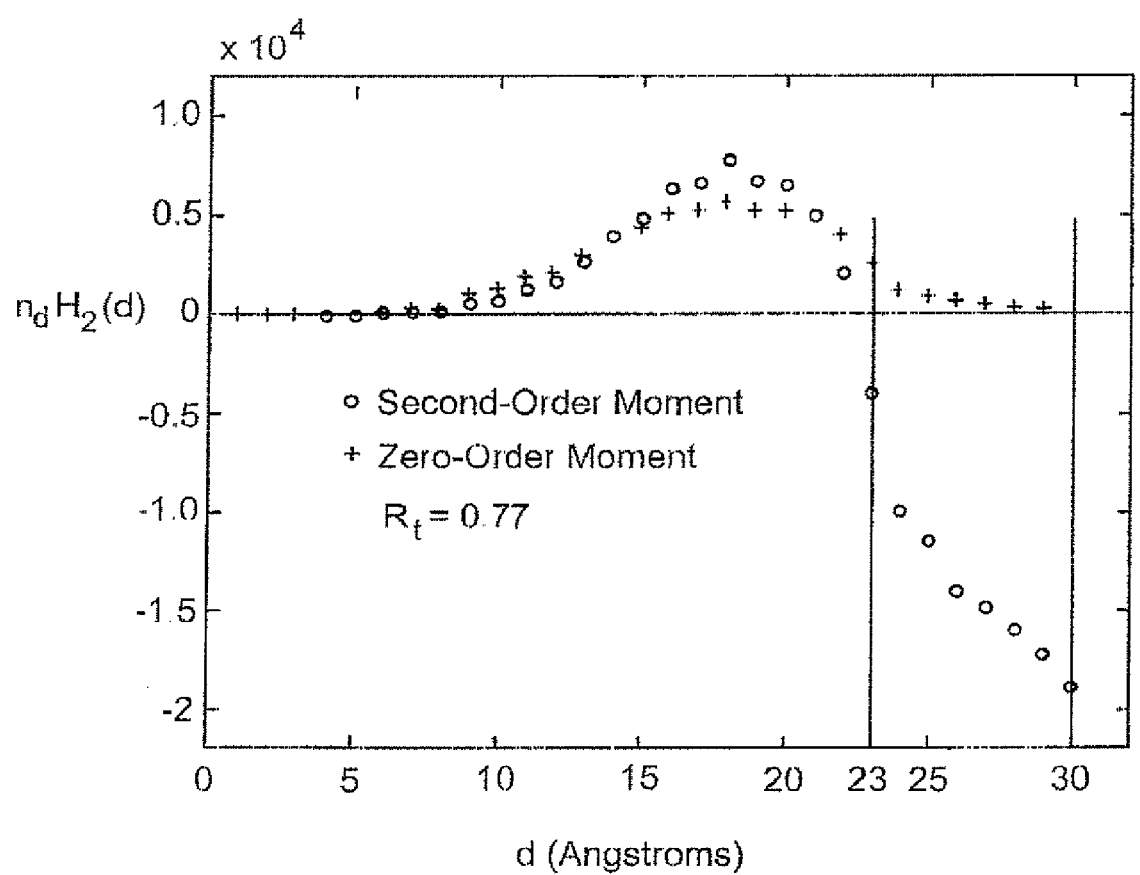
FIG. 5 is a profile showing the second-order moment, determined through use of an embodiment of the present invention, for the 1AKZ protein.

Detailed results of profiling one of the structures, 1AKZ, are shown in FIGS. 5 and 6. FIG. 5 shows the profile of the accumulated zero-order moment, $H_0(d)$, and second-order moment, $H_2(d)$. FIG. 6 lists the moments per residue for $H_0(d)$ and for $H_2(d)$. As the distance, d, that defines the extent of the ellipsoid is increased, the first residue falls within the ellipsoidal surface at a value of d equal to 4 Angstroms. From FIG. 5, one sees the second-order moment increase in value until it turns around, rapidly becoming negative. At the one-Angstrom resolution of the calculation shown in FIG. 6, the first negative value appears at d. equal to 23. The hydrophobicity, of the protein becomes zero at $d_0$ equal to 30. The hydrophobic-ratio, Rt, has a value, therefore, of 23/30 equal to 0.77. The steep decrease of the ellipsoidal moment tapers off in the final range of 25 to 30 Angstroms. Both zero- and second-order moments peak at the same value of d and this distance, at which the maximum occurs, can also be used as a feature for comparison between different proteins.

Figure 7:
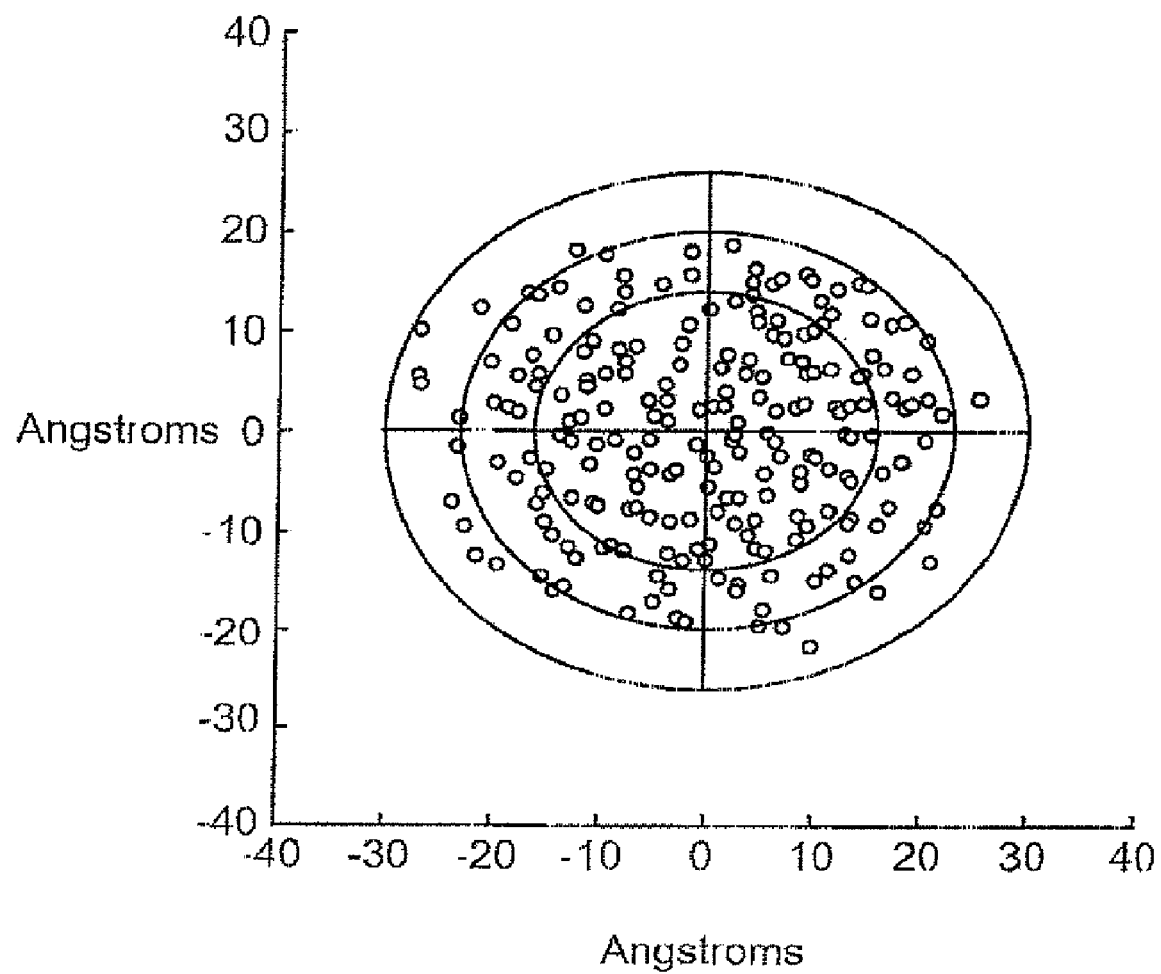
FIG. 7 is a profile showing a view along one principal axis of the 1AKZ protein.

FIG. 7 shows a view along one of the three principal axes of the protein 1AKZ. The projections of the amino acid centroids have been plotted as well as the elliptical boundaries in the plane containing two of the principal axes. The ellipses have been plotted for the value d equal to 16, where the second-order moment is greatest, the value of d. equal to 23, the value at which $H_2$ has just changed sign and the value $d_0$ equal to 30, the value for which all amino acid residue centroids just fall within the ellipsoidal surface. The latter is the point where the protein hydrophobicity vanishes. The region of increasing $H_2$ reflects the predominance of the spatial distribution of residues comprising the hydrophobic core. At larger values of d, the slowing of this increase and plunge to negative values reflects the spatially increasing prevalence of hydrophilic residues. Such regular behavior is required for the identification of d. and consequently for the calculation of Rt. Keeping the 1AKZ structure fixed and randomly shuffling the hydrophobicity values among the different residues yields the results shown in FIG. 8. It is evident from examination of this table that a value of d. cannot be assigned from this distribution of values of the second-order moment.

Figure 9:
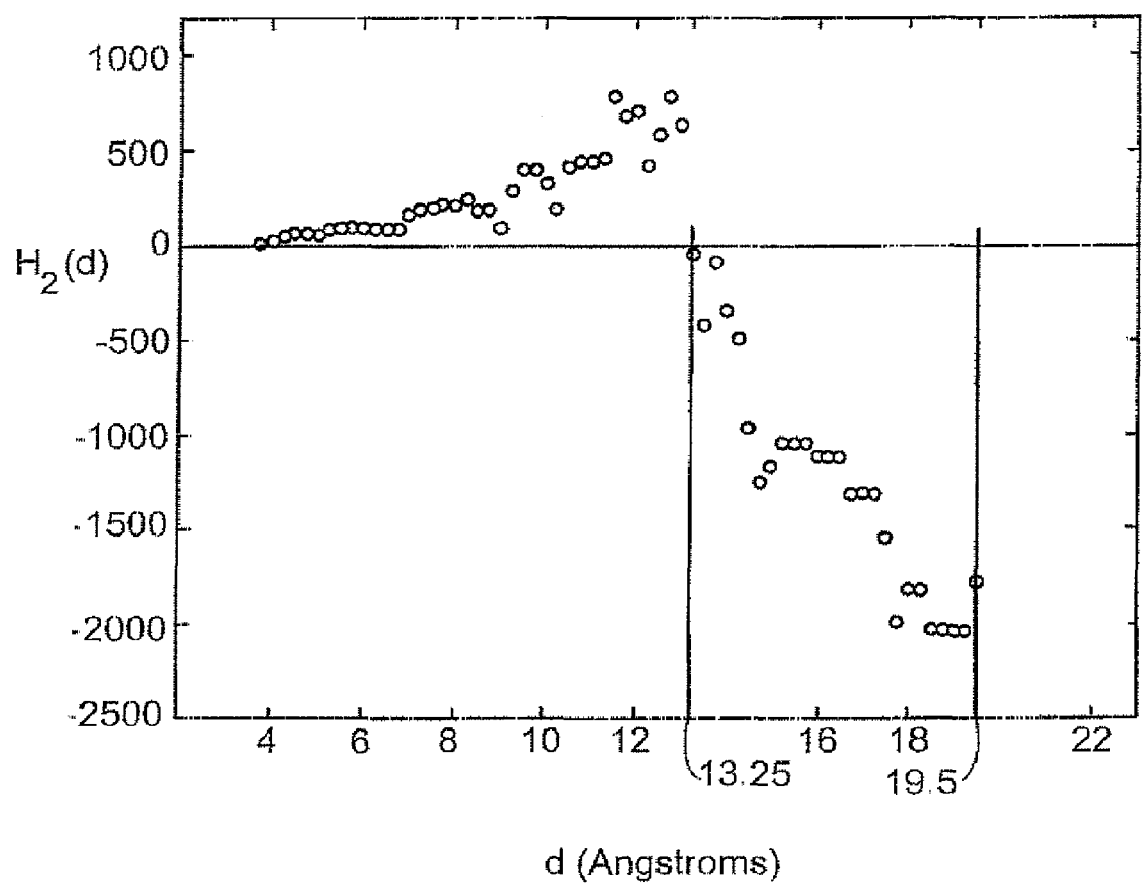
FIG. 9 shows a profile of results, obtained through use of an embodiment of the present invention, for the smallest protein 1ORC.
Figure 10:
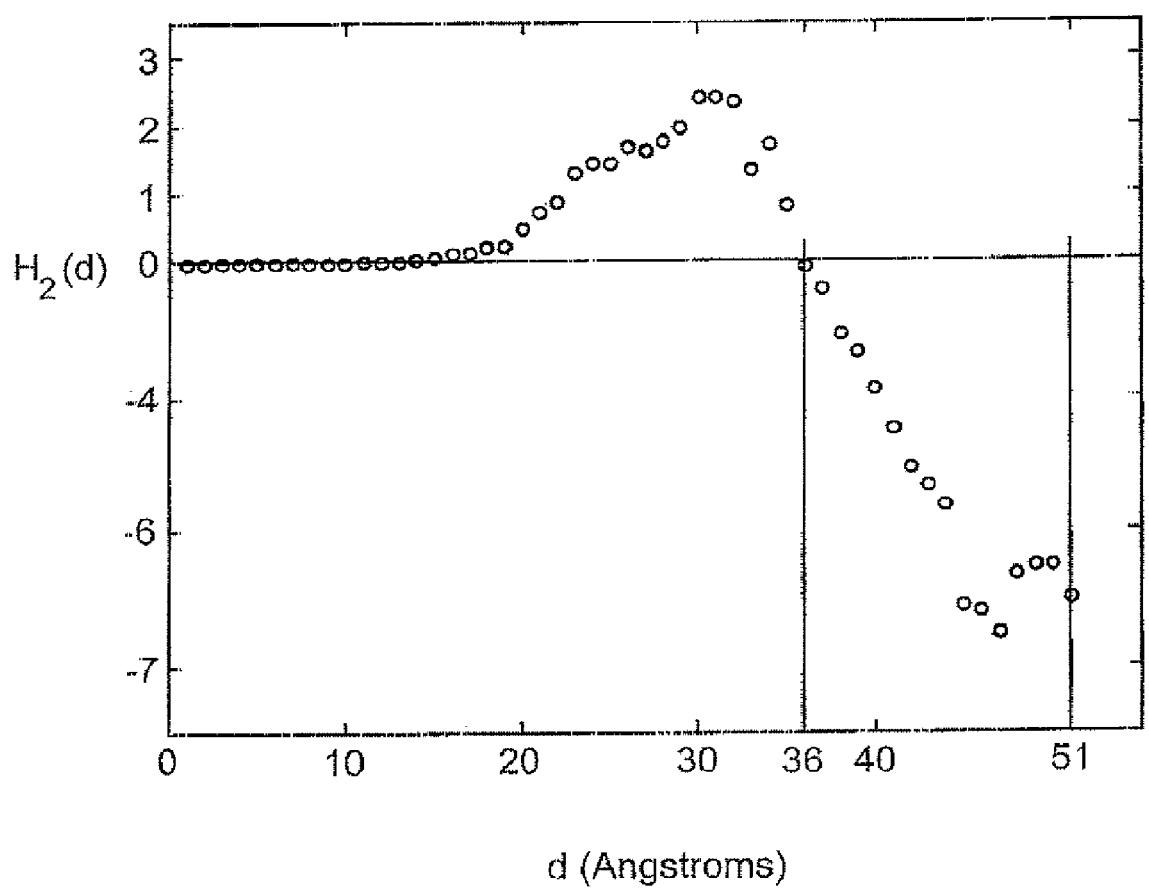
FIG. 10 shows a profile of results, obtained through use of an embodiment of the present invention, for the largest protein 1FEH.

FIGS. 9 and 10 show the second-order ellipsoidal moment profiles obtained for the smallest protein, 1ORC, and the largest protein, 1FEH. 1ORC has been profiled with a resolution of 0.25 Angstroms in FIG. 10. At this resolution, Rt is equal to 0.68. Even though the scales of the axes of both figures differ significantly, the overall profile shapes over the extent of the proteins are similar. Again, there is an initial increase in the value of the second-order moment before plunging to negative values. The hydrophobic ratios, $R_t$, of 1ORC and 1FEH are 0.70 and 0.71, respectively, for the one Angstrom resolution used to obtain the entries listed in FIG. 11. These two example proteins highlight the relative independence of the overall second-order moment profile shape and hydrophobic-ratio with respect to differences in protein size.

All thirty protein structures that were tested exhibit similar spatial behavior for either the accumulated second-order hydrophobic moment, $H_2(a)$, or $H_2^d(d)$, the moment per residue. The accumulated profiles awe, however; somewhat smoother and accentuate the plunge to negative values as the surface of the protein is approached. FIG. 11 lists the value of the hydrophobic-ratio for each of the protein structures. All thirty structures yield a mean value of the ratio equal to 0.75, with a standard deviation of 0.045. The numerator and denominator of Rt, d and $d_0$, are also listed. This clearly shows how d. increases with increasing protein size to provide comparable values of the ratio for all thirty proteins. The value of $d_0$ scales roughly as a factor of two between the largest and smallest proteins examined. This is as expected, since the ratio of the number of amino acid residues of the largest to smallest protein structures is approximately equal to 600/70, and, consequently, $(600/70)^{1/3} \approx 2$. The distance $d_0$ can be considered an approximate measure of the linear extent of the protein. Consequently, the values of d. are then equal to a comparable fraction of the extent of each of the proteins, for all of the structures.

FIG. 11 also shows the results of profiling the distribution with a spherical instead of ellipsoidal contour. The crossover between the positive and negative values of $H_2$ is still well defined. Consequently, a value for the hydrophobic-ratio, Rt, can be calculated. It can be noted that there is greater variability in the hydrophobic-ratio with spherical profiling.

Figure 12:
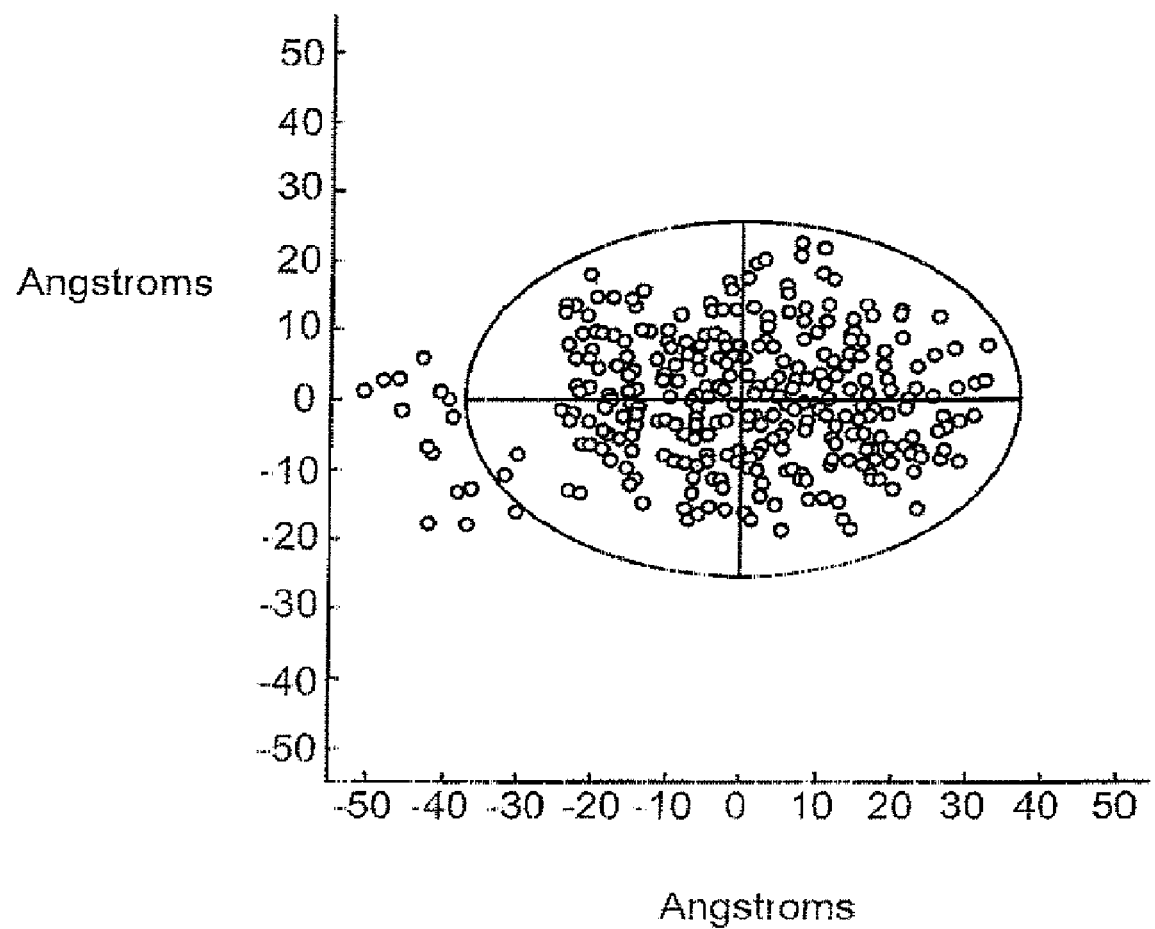
FIG. 12 shows a profile of a view along one of the principal axes of the protein 1LDM, with the ellipsoid intercept in the plane of the two other principal axes.

A few of the proteins require special attention. Three of the structures, 1PDO, 1LDM and 1FSZ, have extended arms that are away from the main body of the protein. Collecting all residues to determine the value of $d_0$ yields a value that is not representative of the protein bulk. Shifting the scale of residue hydrophobicity such that the net hydrophobicity of the protein is zero when all residues of the bulk are collected, yields the values given in FIG. 11. FIG. 12 shows a view along one of the principal axes of 1LDM with the ellipsoidal intercept in the plane of the two other principal axes. The intercept has been drawn for the value, d equal to 37, a value that does not include the contribution from the structural arm.

Structure 1LBU exhibits slightly deviant behavior of $H_2$. There is a rapid crossover to a negative value of the second-order moment at a value of d equal to 20. This value remains negative, until at d equal to 23 it becomes marginally positive before becoming negative again at d equal to 24 and thereafter. The two zero crossovers at d equal to 20 and d equal to 24 yield a hydrophobic-ratio average of 0.76.

Two of the ribosomal proteins, B__1FJF (chain B; protein S2) and D__1FJF (chain D; protein S4) axe the largest deviants with respect to the values of Rt for the non-ribosomal proteins. On the other hand, C__1FJF (Chain C; protein S3) yields a value of Rt that is within the range of the other thirty values C__1FJF makes no contact with RNA at all and exhibits an α/β-domain frequently found in different proteins with α-helices packed against a β-sheet.

Figure 13:
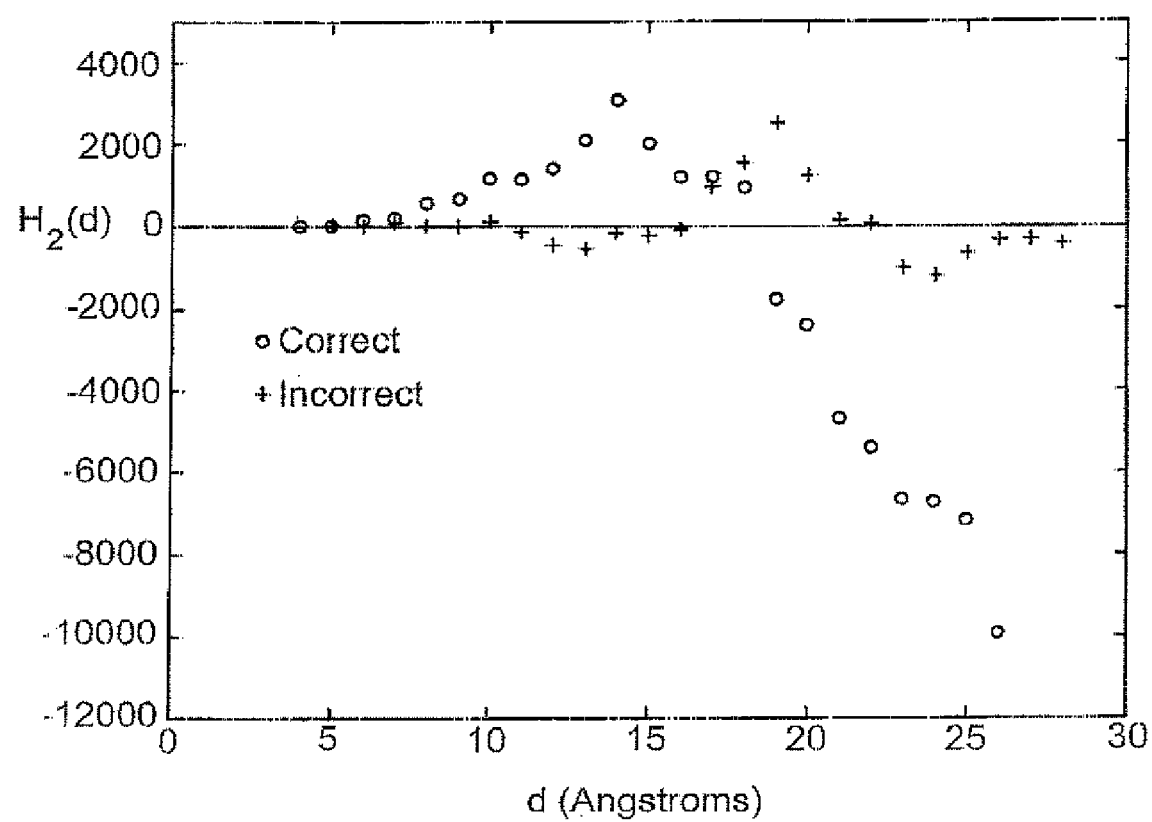
FIG. 13 shows a profile of typical results, obtained through use of an embodiment of the present invention, for a man-made protein structure (a "decoy")

Finally, ellipsoidal moment profiling has been performed on a simple decoy set. Fourteen decoys and native structures of this set, with a number of residues greater than one hundred, were obtained from Stanford University Twenty-eight moment calculations were, therefore, performed. A typical result is shown in FIG. 13. Visual inspection of the figure clearly delineates the difference between the correct or native structure and the decoy structure. Figures for all of the fourteen structures look essentially the same. All native structures exhibit a second-order moment profile similar to what had been obtained for the thirty PDB structures. Consequently, hydrophobic ratios can be calculated and they span the range of values previously found for the thirty. The spatial transition to the hydrophilic exterior of the native structures is significantly amplified by the second-order moment. The decoys do not exhibit this plunge to negative values of the second-order moment, nor is the relatively regular behavior in the protein interior reproduced. Hydrophobic ratios cannot, therefore, be assigned to any of the decoy structures.

The comparison between the second-order moment profiles of the native with the decoy structures is revealing. The second-order moment amplifies differences about the mean protein hydrophobicity. Profiles of the native structures reflect the significant separation between the hydrophobic residues comprising the core and the hydrophilic residues the protein exterior. The decoy residue distribution fails to mirror this separation. This suggests that moment profiling should play an important role in recognizing the difference between native folds and decoy folds. It should also play a role in validating predicted protein structures.

With respect to molecular dynamics and protein folding pathways, profiling could be done at various points in the folding trajectory. One would then look for trajectories that begin to exhibit a relatively smooth monotonic increase of the second-order moment in the structural interior with the onset of a transition to negative values near the exterior. It would then be of interest to see how close such identification would appear with respect to the final native structure achieved. After identification or selection of such trajectory, fine-tuning could then be observed or directed by examination of the hydrophobic-ratio. Considering the native structure as the endpoint in the folding trajectory, perhaps the moment regularities will provide not only constraints with respect to the pathways selected but also provide a clue to the underlying processes responsible for such selection.

The procedures described in this disclosure need not be restricted to examination of globular proteins, but can be used in connection with the profiling of proteins of diverse overall structure with the choice of an appropriate overall profiling geometry.

Thus, what has been shown are techniques for determining profiles and ratios for protein probing and analysis. In the case of globular proteins, heretofore unseen characteristics and similarities between relatively diverse proteins have been shown. Moreover, the present invention allows decoy and unrelated proteins to easily be excluded from a group of already examined and similar proteins.

It is to be understood that the embodiments and variations shown and described herein are merely illustrative of the principles of this invention and that various modifications may be implemented by those skilled in the art without departing from the scope and spirit of the invention. For instance, surfaces other than an ellipse, such as a conical surface or cylindrical surface could be used. Additionally, shifting could be used without normalization.

What is claimed is:

1. A method for spatially profiling a protein to determine if the protein is a globular protein, the method comprising the steps of:
    determining a shifted and normalized hydrophobicity distribution for a protein, wherein determining the shifted and normalized hydrophobicity distribution for a protein is carried out by a component executing on a hardware processor;
    determining a centroid of the protein, wherein determining the centroid of the protein is carried out by a component executing on a hardware processor;
    determining, by using the shifted and normalized hydrophobicity distribution, an adjusted second-order moment of hydrophobicity, wherein determining the adjusted second-order moment of hydrophobicity is carried out by a component executing on a hardware processor;
    determining a profile of the adjusted second-order moment of hydrophobicity, wherein a profile comprises a reference point, a coordinate system and a shape representative of the protein, wherein the reference point comprises the centroid, and wherein determining the profile comprises determining a first distance from the centroid at which the adjusted second-order moment of hydrophobicity is zero, and wherein determining the profile of the adjusted second-order moment of hydrophobicity is carried out by a component executing on a hardware processor; and
    comparing the profile to a globular protein profile to determine if the protein is a globular protein, wherein comparing the profile to a globular protein profile to determine if the protein is a globular protein is carried out by a component executing on a hardware processor.

2. The method of claim 1, wherein:
the step of determining a shifted and normalized hydrophobicity distribution comprises the steps of:
    determining a residue center for each of a plurality of residues of the protein;
    assigning each residue a hydrophobicity value, where a hydrophobicity value is assigned to a corresponding one of the residue centers;
    shifting each the hydrophobicity values of the hydrophobicity distribution such that a total hydrophobicity of the protein is zero; and
    normalizing each of the shifted hydrophobicity values, wherein the hydrophobicity distribution comprises the shifted and normalized hydrophobicity values, which thereby causes a standard deviation of the hydrophobicity distribution to be unity.

3. The method of claim 1, further comprising the steps of:
determining, by using the shifted and normalized hydrophobicity distribution, an adjusted zero-order moment of hydrophobicity;
determining a second distance from the centroid at which the adjusted zero-order moment of hydrophobicity is zero; and
determining a ratio between the first distance and the second distance.

4. The method of claim 3, wherein:
the step of a determining a first distance from the centroid at which the adjusted second-order moment of hydrophobicity is zero comprises the step of determining a surface enclosing an interior volume wherein any larger of a surface will yield a negative adjusted second-order moment of hydrophobicity; and
the step of determining a second distance from the centroid at which the adjusted zero-order moment of hydrophobicity is zero comprises the step of increasing the volume enclosed by the surface until the net hydrophobicity of the protein is zero.

5. The method of claim 1, wherein the step of profiling an adjusted second-order moment of hydrophobicity further comprises the step of determining a profile of the adjusted second-order moment of hydrophobicity with distance from the centroid.

6. The method of claim 1, wherein the step of determining a centroid of the protein comprises the steps of:
- determining a residue center for each of a plurality of residues of the protein;
- assigning each of the residue centers a mass value of one; and
- determining a center of mass of the protein by using the residue centers and the mass value of one at each residue centroid.

7. The method of claim 6, wherein the step of determining a residue center comprises, for each residue in the protein:
- determining a location of each atom in the residue;
- assigning a mass value of one to each location; and
- determining a center of mass of the residue by using the locations of each atom and the mass value of one at each location.

8. The method of claim 6, wherein the step of determining a residue center comprises, for each residue in the protein, determining an alpha carbon atom location.

9. A system for spatially profiling a protein to determine if the protein is a globular protein, comprising:
- a memory that stores computer-readable code; and
- a processor operatively coupled to the memory, the processor configured to implement the computer-readable code, the computer-readable code configured to:
  - determine a shifted and normalized hydrophobicity distribution for a protein;
  - determine a centroid of the protein;
  - determine, by using the shifted and normalized hydrophobicity distribution, an adjusted second-order moment of hydrophobicity;
  - determine a profile of the adjusted second-order moment of hydrophobicity, wherein a profile comprises a reference point, a coordinate system and a shape representative of the protein, wherein the reference point comprises the centroid, and wherein determining the profile comprises determining a first distance from the centroid at which the adjusted second-order moment of hydrophobicity is zero; and
  - compare the profile to a globular protein profile to determine if the protein is a globular protein.

10. The system of claim 9, wherein the computer-readable code is further configured to:
- determine, by using the shifted and normalized hydrophobicity distribution, an adjusted zero-order moment of hydrophobicity;
- determine a second distance from the centroid at which the adjusted zero-order moment of hydrophobicity is zero; and
- determine a ratio between the first distance and the second distance.

11. The system of claim 10, wherein:
- the computer-readable code is further configured, when determining a first distance from the centroid at which the adjusted second-order moment of hydrophobicity is zero, to determine a surface enclosing an interior volume wherein any larger of a surface will yield a negative adjusted second-order moment of hydrophobicity; and
- the computer-readable code is further configured, when determining a second distance from the centroid at which the adjusted zero-order moment of hydrophobicity is zero, to increase the volume enclosed by the surface until the net hydrophobicity of the protein is zero.

12. The system of claim 9, wherein:
- the computer-readable code is further configured, when determining a shifted and normalized hydrophobicity distribution, to:
- determine a residue center for each of a plurality of residues of the protein;
- assign each residue a hydrophobicity value, where a hydrophobicity value is assigned to a corresponding one of the residue centers;
- shift each the hydrophobicity values of the hydrophobicity distribution such that a total hydrophobicity of the protein is zero; and
- normalize each of the hydrophobicity values, wherein the hydrophobicity distribution comprises the shifted and normalized hydrophobicity values, which thereby causes a standard deviation of the hydrophobicity distribution to be unity.

13. The system of claim 9, wherein:
the computer-readable code is further configured, when profiling an adjusted second-order moment of hydrophobicity, to determine a profile of the adjusted second-order moment of hydrophobicity with distance from the centroid.

14. The system of claim 9, wherein:
the computer-readable code is further configured, when determining a centroid of the protein, to:
- determine a residue center for each of a plurality of residues of the protein;
- assign each of the residue centers a mass value of one; and
- determine a center of mass of the protein by using the residue centers and the mass value of one at each residue centroid.

15. The system of claim 14, wherein:
the computer-readable code is further configured, when determining a residue center, for each residue in the protein, to:
- determine a location of each atom in the residue;
- assign a mass value of one to each location; and
- determine a center of mass of the residue by using the locations of each atom and the mass value of one at each location.

16. The system of claim 14, wherein:
the computer-readable code is further configured, when determining a residue center, for each residue in the protein, to determine an alpha carbon atom location.

17. An article of manufacture for spatially profiling a protein to determine if the protein is a globular protein, comprising:
- a computer-readable medium having computer-readable code embodied thereon, the computer-readable code comprising:
  - a step to determine a shifted and normalized hydrophobicity distribution for a protein;
  - a step to determine a centroid of the protein;
  - a step to determine, by using the shifted and normalized hydrophobicity distribution, an adjusted second-order moment of hydrophobicity;
  - a step to determine a profile of the adjusted second-order moment of hydrophobicity, wherein a profile comprises a reference point, a coordinate system and a shape representative of the protein, wherein the reference point comprises the centroid, and wherein determining the profile comprises determining a first distance from the centroid at which the adjusted second-order moment of hydrophobicity is zero; and
  - a step to compare the profile to a globular protein profile to determine if the protein is a globular protein.

18. The article of manufacture of claim 17, wherein the computer-readable code further comprises:
- a step to determine, by using the shifted and normalized hydrophobicity distribution, an adjusted zero-order moment of hydrophobicity;
- a step to determine a second distance from the centroid at which the adjusted zero-order moment of hydrophobicity is zero; and
- a step to determine a ratio between the first distance and the second distance.

19. The article of manufacture of claim 18, wherein:
the computer-readable code further comprises, when determining a first distance from the centroid at which the adjusted second-order moment of hydrophobicity is zero, a step to determine a surface enclosing an interior volume wherein any larger of a surface will yield a negative adjusted second-order moment of hydrophobicity; and
the computer-readable code further comprises, when determining a second distance from the centroid at which the adjusted zero-order moment of hydrophobicity is zero, a step to increase the volume enclosed by the surface until the net hydrophobicity of the protein is zero.

20. The article of manufacture of claim 17, wherein:
the computer-readable code further comprises, when determining a shifted and normalized hydrophobicity distribution:
- a step to determine a residue center for each of a plurality of residues of the protein;
- a step to assign each residue a hydrophobicity value, where a hydrophobicity value is assigned to a corresponding one of the residue centers;
- a step to shift each the hydrophobicity values of the hydrophobicity distribution such that a total hydrophobicity of the protein is zero; and
- a step to normalize each of the hydrophobicity values, wherein the hydrophobicity distribution comprises the shifted and normalized hydrophobicity values, which thereby causes a standard deviation of the hydrophobicity distribution to be unity.

21. The article of manufacture of claim 17, wherein:
the computer-readable code further comprises, when profiling an adjusted second-order moment of hydrophobicity, a step to determine a profile of the adjusted second-order moment of hydrophobicity with distance from the centroid.

22. The article of manufacture of claim 17, wherein:
the computer-readable code further comprises, when determining a centroid of the protein:
- a step to determine a residue center for each of a plurality of residues of the protein;
- a step to assign each of the residue centers a mass value of one; and
- a step to determine a center of mass of the protein by using the residue centers and the mass value of one at each residue centroid.

23. The article of manufacture of claim 22, wherein:
the computer-readable code further comprises, when determining a residue center:
- a step to determine a location of each atom in the residue;
- a step to assign a mass value of one to each location; and
- a step to determine a center of mass of the residue by using the locations of each atom and the mass value of one at each location.

24. The article of manufacture of claim 22, wherein the computer-readable code further comprises, when determining a residue center, for each residue in the protein, a step to determine an alpha carbon atom location.

* * * * *